United States Patent [19]
Larkin

[11] Patent Number: 4,834,992
[45] Date of Patent: * May 30, 1989

[54] NON-TOXIC ORGANOTIN STABILIZERS FOR VINYL CHLORIDE POLYMERS

[75] Inventor: William A. Larkin, Morristown, N.J.

[73] Assignee: M&T Chemicals, Inc., Rahway, N.J.

[ * ] Notice: The portion of the term of this patent subsequent to May 30, 2006 has been disclaimed.

[21] Appl. No.: 13,211

[22] Filed: Feb. 6, 1987

Related U.S. Application Data

[60] Division of Ser. No. 449,085, Dec. 13, 1982, abandoned, which is a continuation-in-part of Ser. No. 120,753, Feb. 12, 1980, Pat. No. 4,496,490, which is a continuation-in-part of Ser. No. 43,997, May 31, 1979, abandoned, which is a continuation of Ser. No. 454,363, Mar. 25, 1974, abandoned, which is a division of Ser. No. 343,648, Mar. 22, 1973, abandoned.

[51] Int. Cl.$^4$ .................... B65D 85/00; C07F 7/22
[52] U.S. Cl. .................... 426/106; 426/131; 426/415; 556/93; 556/96; 556/97; 556/102

[58] Field of Search .................... 426/106, 131, 415

[56] References Cited

U.S. PATENT DOCUMENTS 3,657,294  4/1972  Gloskey .................... 556/88

OTHER PUBLICATIONS

Neumann, the Organic Chemistry of Tin, John Wiley & Sons, Interscience Publ. N.Y., pp. 230–237 & 240–242 (1970).

*Primary Examiner*—Curtis R. Davis
*Attorney, Agent, or Firm*—Burns, Doane, Swecker & Mathis

[57] ABSTRACT

Organotin stabilizer compositions containing more than 5 percent by weight of monoalkyl tin derivatives of mercaptoacetic acid esters, such as mono-n-octyltin-S,S',S''-tris(isooctyl mercaptoacetate), are useful as food-grade stabilizers for vinyl halide polymers.

20 Claims, No Drawings

NON-TOXIC ORGANOTIN STABILIZERS FOR VINYL CHLORIDE POLYMERS

CROSS REFERENCE TO RELATED APPLICATIONS

This application is division of Ser. No. 449,085, filed Dec. 13, 1982, now abandoned, which is a continuation-in-part of application Ser. No. 120,753, filed Feb. 12, 1980, now U.S. Pat. No. 4496,490, which is, in turn, a continuation-in-part of application Ser. No. 043,997, filed May 31, 1979 and now abandoned, which is, in turn, a continuation of application Ser. No. 454,363, filed Mar. 25, 1974, now abandoned, which is, in turn, a divisional of application Ser. No. 343,648, filed Mar. 22, 1973 and now abandoned.

BACKGROUND OF THE INVENTION

This application relates to non-toxic organotin stabilizers. More particularly, this invention relates to organotin stabilizer compositions that contain at least one mono-n-octyltin mercaptoacetic acid ester for halogen-containing polymers that are sufficiently low in toxicity to be suitable for use in packaging materials for food and beverages.

Polymer compositions derived from halogen-containing monomers such as vinyl chloride and vinylidene chlorine are unstable when exposed to temperatures above about 100° C. for the time periods required to process these polymers into shaped articles such as films and containers. A variety of compounds has been developed which effectively prevent or delay the discoloration and embrittlement that attend vinyl chloride polymers processed at these temperatures. Some of these stabilizers are of low toxicity, a discovery that has facilitated the use of vinyl chloride polymers as food packaging materials; such use may take the form of films, bottles, trays and containers.

Organotin compounds containing sulfur have long been recognized as effective stabilizers for vinyl halide homopolymers and copolymers. U.S. Pat. No. 2,789,963 discloses organotin compounds suitable for this purpose. Diorganotin dimercaptides and bis(mercapto-carboxylic acid esters) are said to be particularly preferred, because of their superior performance. However, a shortcoming of many of these sulfur-containing organotin compounds, which can be represented by the general formulae $R_2Sn(SR')_2$ and $R_2Sn(SR''COOR')_2$, wherein R and R' represent monovalent hydrocarbon radicals and R" represents a divalent hydrocarbon radical, is that they are too toxic for use in food packaging materials.

The use of di-n-octyltin-S,S'-bis(isoctyl mercaptoacetate) as a food grade stabilizer for vinyl chloride polymers is disclosed in U.S. Pat. No. 3,640,947. This patent teaches that the stabilizer is prepared from a di-n-octyltin oxide composition containing not more than 5% by weight of an n-octylstannoic acid, the precursor of mono-n-octyltin-S,S',S"-tris(isooctyl mercaptoacetate). It was believed necessary to limit the concentration of mono-and/or tri-n-octyltin compounds to less than 5%. A related U.S. Pat. No. 3,390,159, discloses a process for preparing di-n-octyltin oxide from di-n-octyltin dichloride in the absence of impurities. These impurities result from the presence, in the crude di-n-octyltin chloride, of mono-n-octyltin trichloride and tri-n-octyltin chloride in addition to inorganic compounds. One reason for excluding mono- and tri-n-octyltin compounds is that they were believed to increase the toxicity of the resultant di-n-octyltin oxide, which is subsequently reacted with an octyl ester of mercaptoacetic acid to obtain the food grade stabilizers.

At present only di-n-octyltin-S,S'-bis(isooctyl mercaptoacetate) and di-n-octyltin maleate polymer have been recognized by the U.S. Food and Drug Administration (FDA) to be sufficiently low in chronic toxicity and extractability from vinyl halide polymers to qualify as a food-grade stabilizer. The FDA specifications for di-n-octyltin-S,S'-bis (isooctyl mercaptoacetate) require that it be prepared from di-n-octyltin dichloride and that the combined concentrations of mono-n-octyltin trichloride and tri-n-octyltin chloride do not exceed 5% by weight of total organotin halides. The di-n-octyltin dichloride is optionally converted to di-n-octyltin oxide before being reacted with isooctyl mercaptoacetate.

Dialkyltin dichlorides, such as di-n-octyltin dichloride, are conventionally prepared by reacting the corresponding tetraalkyltin compound, such as tetra-n-octyltin, with stannic chloride using equimolar amounts of the two reagents. However, the reaction of a tetraalkyltin compound with stannic chloride produces equilibrium mixtures containing substantial amounts of mono-, and triorganotin chloride, requiring considerable purification to reduce the mono- and tri- species to less than 5%.

The toxicity of a given tin compound cannot be readily predicted. That the determination of toxicity values for tin compounds is both empirical in nature and unpredictable, and that available data is contradictory is apparent from two papers, one an independent study by Luijten and Klimmer, "A Toxological Evaluation of the Organotin Compounds", Tin Research Institute, Fraser Road, Perivale, Greenford, Middlesex. Revised version of a paper presented at the 18th German tin meeting: "Tin in Chemistry-organic and inroganic tin compounds" of the Zin Informationsburo GmbH, Dusseldorf, on Nov. 15, 1973 at VDI-Hause, Dusseldorf. The other paper is by Pelikan and Cerny, "The Toxic Effects of Some Di- and Mono-n-octyltin Compounds on White Mice", Arch. Toxikol. 26, (3) 196–202 (1970).

The study by Luijten et al. shows that for n-octyltin chlorides toxicity, as measured by $LD_{50}$, is most pronounced for the mono-n-octyl compound, less for the di-n-octyl compound, and least for the tri-n-octyl compound. This order of toxicity, however, does not follow when n-octyl tin isooctyl mercaptoacetates are compared; in this case the tri-octyl species is again, unexpectedly, the least toxic, followed by the mono-n-octyl compound. The di-n-octyl compound is the most toxic. However, Pelikan et al. show that when n-octyltin 2-ethylhexyl mercaptoacetate $LD_{50}$ values are compared for white mice, the mono-n-octyl species is more toxic than the di-n-octyl compound.

For a material to qualify as a food grade additive it must not present any toxicity hazard at the highest concentration level at which it will be present in the food packaging material. The criteria for determining whether a given ingredient in a plastic material constitutes a toxicity hazard have been defined by the United States Food and Drug Administration (FDA). These criteria are set forth in a comprehensive article that appeared in the October, 1955 issue of the Food Drug Cosmetic Law Journal, and can be summarized as follows:

(1) An ingredient of a plastic material which is not extracted by a foodstuff with which it is in contact does not constitute a hazard.

(2) If a material is found in a food as a result of contact with a plastic, that material may constitue a toxic hazard if it is toxic in the biological sense, i.e. if it causes either an acute or chronic injurious effect by oral ingestion, inhalation, or absorption through the skin, in animals or humans. If no such effect can be shown the material does not constitute a hazard.

(3) Acute toxic levels are unlikely ever to be realized in practice. It is, however, possible that injurious effects may be produced by repeated small doses of a material extracted from a plastic and therefore it is chornic toxicity which should be used for the purpose of assessing the hazard.

(4) The toxic hazard of an ingredient of a plastic material is a function both of its chronic toxicity and of its extractability from the plastic material under service conditions.

(5) For the purpose of assessment of the hazard, extractability tests must be carried out using the foodstuffs themselves or a range of representative extractants under conditions which simulate the most severe conditions likely to be encountered in practice. The results of these tests must then be combined with the data on the chronic toxicities of the ingredients of the plastic as expressed by their Toxicity Factors to give the Toxicity Quotient, which is the measure of the hazard.

To have a composition approved by the FDA and other national health authorities as a food-grade additive, an applicant must submit data from feeding studies on laboratory animals demonstrating that daily consumption of the candidate composition over an extended period of time at concentration levels above those that would be expected based on extractability of the composition from the packaging material does not noticeably impair the health of the animals or result in a significant accumulation of test compound in the blood, bones and internal organs. Since the prior art considers mono-n-octyltin compounds to be undesirable contaminants in a food grade di-n-octyltin stabilizer composition, and limits the maximum concentration thereof to 5% by weight, there is no incentive provided to undertake the extensive feeding and extraction studies required to determine whether the mono-n-octyl compounds would be useful as food-grade stabilizers.

It was surprising to discover that mono-n-octyltin- S, S',S''-tris(isooctyl mercaptoacetate) is actually less toxic than the corresponding di-n-octyltin compound already approved by the FDA as a food grade stabilizer, and that the extractability values for the two compounds are equivalent.

SUMMARY OF THE INVENTION

This invention relates to the discovery that mono-n-octyltin compounds are sufficiently low in toxicity to be useful as food-grade stabilizers by themselves, or in combination with other food grade stabilizers, for vinyl halide polymer compositions. In one aspect, the invention relates to a food grade organotin stabilizer composition for food grade vinyl halide polymer compositions which contains more than 5 percent by weight of a mono-n-octyltin compound, and, preferably, is characterized by (a) an acute toxicity value for rats and dogs, expressed as $LD_{50}$, greater than 1.00 gram per kilogram of body weight.

(b) an extractability from polyvinyl chloride by heptane of less than 0.05 milligram per square decimeter of exposed surface or an extractability from polyvinyl chloride by foodstuffs of less than 1 part per million (ppm).

In another aspect, the mono-n-octyltin compound has the formula

$$n\text{-}C_8H_{17}Sn(SCH_2COOR)_3$$

where R is a linear or branched alkyl group of 8 carbon atoms.

In yet another aspect the organotin stabilizer composition contains in addition to the monooctyltin compounds other food grade stabilizers such as the di-n-octyltin compounds.

DETAILED DESCRIPTION OF THE INVENTION THE FOOD GRADE STABILIZER COMPOSITIONS

The food grade organotin stabilizer compositions of this invention contain at least 5 percent by weight and, preferably, at least about 30 percent by weight based on the weight of organotin compounds of at least one mono-n-octyltin compound. The mono-n-octyltin compounds can be represented by the general formula

$$n\text{-}C_8H_{17}Sn(SCH_2COOR)_3.$$

In this formula, R represents an alkyl group containing eight carbon atoms, which can be in a linear or branched configuration. This group represents the hydrocarbon residue of the alcohol employed to prepare the mercaptoacetic acid ester that is subsequently reacted with a mono-n-octyltin halide or n-octylstannoic acid to obtain the final mono-n-octyltin stabilizer. Thus, R can be one or more of n-octyl or any of the isomeric methylheptyl or ethylhexyl groups. The alkyl group, represented by R can contain 2 or more branching groups, such as would be present in 2-methyl-3-ethylpentanol. R can represent different eight carbon alkyl groups.

A conveniently available branched group is 2-ethylhexyl, based on the commercial availability of 2-ethylhexanol.

In another embodiment, R can be obtained from the mixture of branched eight carbon alkyl groups present in a product referred to by commercial sources as "isooctanol" that has been prepared by the so-called "Oxo" process. In accordance with this process, which is actually a hydroformylation reaction followed by a reduction, one or more olefins containing seven carbon atoms is reacted with hydrogen and carbon monoxide. The product of this reaction is a mixture of aldehydes that is subsequently reduced to the corresponding alcohols. Commercially produced isooctanol may contain 3 or more isomeric dimethylhexanols, 3 or more methylheptanols and various isomeric ethylmethylpentanols. The reaction of this mixture of alcohols with mercaptoacetic acid yields a commercially produced ester identified as "isooctyl mercaptoacetate". The mono-n-octyltin derivative of this ester is a preferred food grade stabilizer; it contains from 13-15% by weight of tin, depending upon the types and amount of impurities present, and is a light yellow liquid at room temperature (i.e. about 25° C.).

The mono-n-octyltin component of the stabilizer composition of this invention can be prepared by reacting a mono-n-octyltin trihalide, n-octyl-stannoic acid or the corresponding anhydride with a mercaptoacetic acid ester of the formula HSCH$_2$COOR, where R is as previously defined.

The reaction between the mercaptoacetic acid ester and an n-octyltin trihalide can be conducted at temperatures between ambient and 100° C.

The two reagents can be reacted in the absence of any diluent, however it has been found desirable to conduct the reaction in a suitable liquid medium in which both reagents are soluble at the reaction temperature. Liquid hydrocarbons containing from 6 to about 8 carbon atoms satisfy this criterion. Cyclohexane is a preferred hydrocarbon, based on the boiling point and other physical properties of this compound. A water-soluble basic compound such as ammonia or an alkali metal hydroxide is usually employed to neutralize the hydrogen halide formed as a byproduct of the reaction.

The reaction between the n-octyltin trihalide, mercaptoacid ester and ammonia can be represented by the following equation:

$$n\text{-}C_8H_{17}SnX_3 + 3HSCH_2COOR + NH_3 \rightarrow n\text{-}C_8H_{17}Sn(SCH_2COOR)_3 + 3NH_4X$$

The resultant halide salt is insolube in the organic phase of the reaction medium, thereby displacing the equilibrium point of the reaction toward formation of the desired mono-n-octyltin derivative of the mercaptoacetic acid ester. The reaction is preferably conducted by gradually adding an aqueous solution of the basic compound to a mixture comprising an n-octyltin trihalide, a suitable mercaptoacid ester and a liquid hydrocarbon. This reaction is often exothermic, in which instance the rate of addition of basic compound is adjusted to maintain the reaction mixture at the desired temperature, which is usually from 30° to about 80° C. The n-octyltin mercaptoacid ester product is isolated from the organic portion of the resultant two-phase reaction mixture. n-Octyltin trichloride is the preferred halide species; this preference is based on the low cost and commercial availability of stannic chloride, the reagent employed to prepare the n-octyltin trichloride.

If n-octylstannoic acid or the corresponding anhydride is used in place of an n-octyltin trihalide, the foregoing reaction conditions can be employed with the exception that no basic compound is required. Heating of the reaction mixture at temperatures up to the boiling point may be required to attain the desired reaction rate.

To maximize product yield it may be desirable that the relative concentration of mercaptoacetic acid ester be slightly in excess of the 3:1 molar ratio required by the stoichiometry of the reaction, as illustrated by the preceding equation.

The n-octyltin trihalide can be prepared by a redistribution or disproportionation type reaction between a stannic halide, preferably the chloride, and tetra-n-octyltin, the latter being the major product obtained from the reaction of an n-octylmagnesium halide with a stannic halide in a molar ratio of 4:1. The conditions for the latter reaction are extensively described in the chemical literature, for example in U.S. Pat. No. 2,675,398.

The organotin stabilizer composition of the invention can contain the mono-n-octyltin compounds alone or in combination with other organotin compounds recognized as acceptable for use in contact with food. Other organotin stabilizers that can be present in the stabilizer compositions of this invention include di-n-octyltin bis(isooctyl mercaptoacetate), the di-n-octyltin maleate polymer and the like.

As previously discussed, the reaction between a tetraorganotin compound and a stannic halide produces an equilibrium mixture of products. The actual product distribution is dependent upon the molar ratio of the two reagents and the reaction conditions. It is possible to adjust the stoichiometry and reaction conditions to obtain mixtures comprising a mono-n-octyltin trihalide and a di-n-octyltin dihalide wherein the di-n-octyltin dihalide constitutes from 25 to 75% by weight of the mixture. In accordance with a preferred method for preparing the present food grade stabilizers, such a mixture of mono- and di-n-octyltin halides is reacted with the mercaptoacid ester without first separating out the di-n-octyltin compound. The concentration of mono-n-octyltin compound in the resultant composition is correspondingly from about 25 to to 75% by weight.

As used in this specification, the term "food-grade stabilizer" refers to compositions exhibiting an acute toxicity (expressed as LD$_{50}$) greater than 1.00 g per kilogram of body weight, and an extractability by heptane from polyvinyl chloride of not more than 0.05mg per square decimeter of exposed surface or by foodstuffs of less than 1 part per million (ppm).

The procedure for determining acute toxicity values by force-feeding specified amounts of the test compound to groups of laboratory test animals such as rats or dogs is well known. These values are usually reported in units of the number of grams or milligrams of test compound per kilogram of body weight that is lethal to 50% of the population. The acute toxicity is usually reported as an acute oral median lethal dose (LD$_{50}$) and is calculated using a method described by C. S. Weil in an article that appeared in the September, 1952 issue of Biometrics.

The no-effect toxicity level of an organotin compound is conventionally determined by conducting relatively long-term feeding studies, usually over a period of several weeks, during which time the test animals are provided with food containing small amounts of the test compound. The general appearance, size, weight and health of the test animals are continuously monitored and the amount of food consumed is recorded. At the end of the test period all surviving animals are sacrificed. Autopsies are performed on all animals, during which the internal organs are examined, weighed and analyzed for tin content; the tin content of the bones, blood and urine is also determined. The no-effect level is the highest concentration of test compound that has no detectable adverse effect on the general health of the animals or the condition of their internal organs as determined using the foregoing procedures.

THE VINYL HALIDE POLYMER

The term "vinyl halide polymer composition" means homopolymers and copolymers derived from a vinyl halide as well as polymer blends containing said homopolymer or copolymer as a component. The homopolymers, copolymers and polymer blends containing a vinyl halide useful in the practice of this invention include for example, (1) polyvinyl chloride, polyvinylidene chloride, polyvinyl bromide, polyvinyl fluoride and polyvinylidene fluoride, (2) copolymers of vinyl chloride with one or more copolymerizable ethylenically unsaturated monomers such as vinylidene chloride, vinyl acetate, vinyl butyrate, vinyl benzoate, diethyl fumarate, diethyl maleate, other alkyl fumarates and maleates, vinyl propionate, acrylic acid, methyl acrylate, 2-ethylhexyl acrylate, butyl acrylate, ethyl acrylate and other alkyl acrylates, methacrylic acid, methyl methacrylate, ethyl methacrylate, butyl methacrylate, hydroxyethyl methacrylate and other alkyl methacrylates, methyl alpha chloroacrylate, styrene, vinyl ethers such as vinyl ethyl ether, vinyl chloroethyl ether and vinyl phenyl ether, vinyl ketones such as vinyl methyl ketone and vinyl phenyl ketone, 1-fluoro,-1-chloroethylene, acrylonitrile, chloroacrylonitrile, allylidene diacetate, chloroallylidene diacetate, olefins such as ethylene and propylene, and (3) polymer blends such as blends of polyvinyl chloride and polyethylene, polyvinyl chloride and polymethyl methacrylate, polyvinyl chloride and polybutyl chloride and acrylonitrile-butadiene-styrene terpolymers and ternary mixtures such as those containing polyvinyl chloride, polyethylene and polymethyl methacrylate.

Typical vinyl halide copolymers applicable for use include vinyl chloride-vinyl chloride-vinyl acetate, vinyl chloride-vinylidene chloride, vinyl chloride-diethyl-fumarate, vinyl chloride-trichloroethylene and vinyl chloride-2-ethylhexyl acrylate. Suitable polymer blends comprise physical blends of at least two or more distinct polymeric species and typically contain from 25 to 95 weight percent of vinyl halide homopolymer or vinyl halide copolymer. The vinyl halide copolymers typically contain from about 25 to about 95 mole percent vinyl halide units.

In preferred embodiments the polymer is a homopolymer or copolymer of vinyl chloride. This preference is based on the lower cost and commercial availability of vinyl chloride relative to other vinyl halides as well as the commercial acceptance of vinyl chloride polymers as food packaging materials.

The benefits of this invention apply to both rigid and flexible vinyl halide polymers

STABILIZED FOOD GRADE POLYMER COMPOSITIONS

The food grade organotin stabilizer composition of the invention, can be generally present in a vinyl halide polymer composition an amount ranging from more than 0.15 to bout 5 parts by weight per 100 parts by weight of vinyl halide polymer composition. If the vinyl halide polymer composition is to be processed at temperatures above about 200° C., it may be desirable to use higher concentrations of stabilizer, e.g. up to about 5 parts per 100 parts of polymer. At about this level the heat stability imparted by the organotin stabilizer composition reaches a maximum and there is no incremental benefit obtained by adding more of this stabilizer. Other stabilizers and boosters can of course be added for enhanced effectiveness.

Use of the food grade organotin stabilizer composition of the invention at a level of from 1 to 4 parts per 100 parts of vinyl halide polymer composition will be more usual because this range affords effective heat stability to vinyl halide polymer compositions that are blow molded to form bottles, that are extruded in the form of films useful to wrap foods, or that are otherwise thermoformed to form containers.

The amount of stabilizer required to effectively stabilize a vinyl halide polymer composition is dependent upon several variables, among which are the heat stability of the unstabilized polymer, processing temperature, length of processing time and the presence of other additives, including heat stabilizers.

The present stabilizer compositions are typically employed at concentrations of from 0.3 to about 5 parts per 100 parts of vinyl halide polymer. The range from about 1 to about 4 parts per 100 parts of polymer is particularly preferred, since this range provides adequate heat stability to vinyl chloride polymer formulations that are suitable either for blow molding under conventional conditions to form bottles or for processing to form food wrapping material or containers.

Other stabilizers that can also be present in the food grade stabilizer compositions of this invention or used in conjunction therewith include the calcium and zinc salts of carboxylic acids containing eight or more carbon atoms. Mixtures comprising calcium and zinc stearates are particularly effective food grade stabilizer for both rigid and plasticized vinyl halide polymers.

When the organotin stabilizer compositions of the invention comprises di-n-octyltin bis(isooctyl mercaptoacetate) in conjunction with the mono-n-octyltin compounds as described herein it is conveniently added in the form of the mixture of mono-n-octyltin and di-n-octyltin compounds obtained when the compounds are synthesized, without intermediate separation. The mixture will generally contain from about 27 to 73% by weight of the di-n-octyltin compound and correspondingly from about 73 to 27% by weight of the mono-n-octyltin compound, and preferably up to about 50 percent by weight of the di-n-octyltin compound, as well as trace amounts of other materials. Thus, the stabilizer composition can contain between about 1 and 100 percent, based upon the weight of the mono-n-octyltin compound of the di-n-octyltin compound. When this mixture is used in an amount of from 0.3 to 5 parts per 100 parts of polymer, the resultant composition will contain from 0.08 to 3.6 parts by weight of mono-n-octyltin compound per 100 parts by weight of polymer. A specific mixture in this range contains 33% by weight of di-n-octyltin compound and 67% by weight of mono-n-octyltin compound; a vinyl halide polymer composition stabilized therewith will contain from 0.1 to 1.7 parts by weight of di-n-octyltin compound per 100 parts of polymer and from 0.2 to 3.4 parts by weight of mono-n-octyltin compound per 100 parts by weight of polymer.

There can also be added auxiliary heat stabilizers which do not impart any appreciable amount of stability when used alone, but act synergistically with many primary stabilizers, including organotin compounds, to increase the level of heat stability imparted by the primary stabilizer. Auxiliary stabilizers that can be incorporated into the food grade polymer compositions of this invention include triesters of phosphorous acid, such as tri(nonylphenyl)-phosphite, polyfunctional alcohols such as mannitol and pentaerythritol and epoxidized oils, such as epoxidized soybean oil.

In addition to one or more heat stabilizers, the present food grade polymer compositions can contain other conventional additives approved for use in food grade polymer compositions. These additives include plasticizers, antioxidants, impact modifiers, pigments, dyes and other coloring materials and compounds that prevent or inhibit degradation of the polymer by untraviolet light. Typical plasticizers, used in amounts of up to about 15% in semi-rigid formulations and about 60% in film, include butylbenzyl phthalate, dioctyl phthalate, dicyclohexyl phthalate, dihexyl phthalate, and di-2- ethylhexyl adipate. Polymer compositions used for blow molding bottles often contain impact modifiers, such as acrylonitrile-butadiene-styrene terpolymers or polymers derived from esters of acrylic or methacrylic acid, in an amount from about 3 to about 20%, based on the weight of the polymer. Typical antioxidants include the hindered phenols, particularly 2,6-di-tert-butyl-p-cresol, and are conventionally used at relatively low concentrations, e.g., 0.1 to 0.2%, based on the weight of the polymer being stabilized.

Compositions containing the vinyl halide polymer, one or more stabilizers and any other desired additives are conveniently prepared by milling, dry or melt blending, or other commonly employed formulation technique which uniformly disperses all the additives, particularly the stabilizer, throughout the polymer composition. Sheet and film products can be prepared using mills, such as 2-roll differential speed mills, calender rolls, as well as by extrusion. Semi-rigid and rigid products can be formed by various known means, including extrusion, injection molding and blow molding.

Stabilized vinyl chloride polymer compositions are useful in the form of films, in the form of bottles, and other packaging items.

EXAMPLE I

Preparation of n-octyltin-S,S',S"-tris(isooctylmercaptoacetate)

A reaction vessel was charged with 750 g of n-octyltin trichloride (99.2% pure), 1387.5 g of isooctylmercaptoacetate and 750 g of cyclohexane. 450 g of an aqueous solution containing 25% by weight of ammonia (calculated as ammonium hydroxide) was gradually added with agitation to the resultant mixture at a rate such that the temperature of the reaction mixture did not exceed 50° C. The contents of the reaction vessel were stirred for one hour following completion of the addition, after which 2,025 g of water were added to dissolve the ammonium chloride formed during the reaction. Following the addition of 750 g of cyclohexane the aqueous portion was separated from the resultant two-phase liquid and discarded. The water and cyclohexane present in the organic portion were removed by distillation under reduced pressure. The resultant almost colorless liquid product was found to contain the following percentage by weight of elements:

tin —13.75% (theoretical=14.12%)
sulfur —11.23% (theoretical=11.42%)

Mono-n-octyltin-S,S',S"-tris(2-ethylhexyl mercapto acetate) can be prepared using the reaction conditions described in this example and substituting an equal weight of 2-ethylhexyl mercaptoacetate for the corresponding isooctyl ester.

Methods for preparing alkyltin trichlorides are described in the prior art, for example in British Pat. No. 739,883.

EXAMPLE II

Part A

This example demonstrates the low degree of extractability from polyvinyl chloride that characterizes the present mono-n-octyltin stabiizers.

A mixture containing 100 parts of a commercially available vinyl chloride homopolymer (Solvic 223), 0.2 part of a half glycol ester, half calcium soap of montanic acid (available as Hoechst Wax OP) together with 1.5 parts of mono-n-octyltin-S,S",S"-tris(isooctyl mercaptoacetate) was blended by placing the components on a 2-roll mill wherein the roll temperature was between 160°and 170° C. During the three minute milling period a continuous sheet formed around one of the rollers was removed. The sheet measured 1.3mm in thickness and about 300cm² in area. The sheet was pressed at a temperature of 170° C. to a thickness of 1.2mm. The total pressing time, including a two minute preheating period, was five minutes. Square samples measuring 30cm² in total surface area were completely immersed in each of the extractants for 10 days, during which time the temperature of the extractant was maintained at 40° C. The extractants employed were distilled water, a 3% aqueous solution of acetic acid, peanut oil and a 10% by weight aqueous solution of of ethanol. With the exception of the peanut oil, a 300cc portion of the extractant was employed for the test. The quantity of peanut oil was 30cc.

The migration of stabilizer from the polyvinyl chloride sample into the extractant was determined by measuring the concentration of tin in the extractant using colormetric analysis of the tin-pyrocatechol violet complex. The method is described by Newman and Jones [Analyst 91 (1966) 406–410]. In no instance did the amount of stabilizer extracted exceed 0.05mg per square decimeter of exposed sample surface area.

Part B

The following procedure was employed to determine the extraction levels from a vinyl chloride homopolymer of mono-n-octyltin-S,S',S"-tris(isooctyl mercaptoacetate), di-n-octyltin-S,S'-bis(isooctyl mercapto- acetate) and a 1:1 weight ratio mixture of these two stabilizers.

A number of 16 ounce (475cc)-capacity cylindrical bottles were prepared by blow molding the following formulation:

| | Parts (by weight) |
|---|---|
| Vinyl chloride homopolymer (Stauffer 608) | 100.0 |
| Acrylic polymer processing aid (Rohm & Haas K-120N) | 3.0 |
| Acrylic polymer impact modifier (Rohm & Haas KM-611) | 12.0 |
| Carboxylic ester wax (Hoechst Wax E) | 1.0 |
| Stabilizer | 3.0 |

The bottles were filled with 450cc of the desired extractant and then placed in an oven maintained at the indicated temperature for the time periods specified in the following table. 200cc of the contents of each bottle were removed and analyzed for tin content. The analysis involves reducing stannic tin to stannous with thioglycollic acid; after adding sodium lauryl sulfate, a dispersing agent, the color forming agent dithiol (toluene-3,4-dithiol) is added. The red reaction product is measured by its light absorption at 530mu on a specrophotometer.

| Extraction Medium | Resident Time | | Tin Content (ppm) | | |
|---|---|---|---|---|---|
| | Hours | Temp °F. | A | B | C |
| Distilled Water | 72 | 120 | 0.0 | 0.0 | 0.0 |
| | 96 | 120 | 0.0 | 0.0 | 0.0 |
| | 129 | 120 | 0.0 | 0.0 | 0.0 |
| 3% Acetic Acid | 24 | 120 | 0.1 | 0.0 | 0.1 |
| | 48 | 120 | 0.2 | 0.0 | 0.0 |

| Extraction | Resident Time | | Tin Content (ppm) | | |
| --- | --- | --- | --- | --- | --- |
| Medium | Hours | Temp °F. | A | B | C |
| | 72 | 120 | 0.1 | 0.0 | 0.1 |
| 8% Ethanol* | 24 | 120 | 0.0 | 0.0 | 0.0 |
| 50% Ethanol* | 24 | 120 | 0.1 | 0.2 | 0.1 |
| | 48 | 120 | 0.1 | 0.3 | 0.1 |
| | 72 | 120 | 0.1 | 0.2 | 0.1 |
| Heptane | 6 | 100 | 0.1 | 0.2 | 0.2 |
| | 8 | 100 | 0.2 | 0.1 | 0.2 |
| | 10 | 100 | 0.2 | 0.1 | 0.2 |

*In an aqueous solution
A - mono-n-octyltin-S,S',S"—tris(isooctyl mercaptoacetate) (<2% of B)
B - di-n-octyltin-S,S'—bis(isooctyl mercaptoacetate) (<2% of A)
C - 1:1 (by weight) ratio mixture of A + B.

The foregoing data demonstrate that the amounts of the three stabilizer compositions extracted are equivalent, and range from 0.00 to 0.3 parts per million. The present stabilizer compositions would therefore not represent a toxicity hazard based on their extractability from polyvinyl chloride by those liquids which they would be most likely to come into contact with when employed as food grade stabilizers.

EXAMPLE III

This example demonstrates the low acute and chronic toxicites of mono-n-octyltin-S,S',S"-tris(isooctyl mercaptoacetate).

Young albino rats were kept under observation for five days prior to commencement of the test. During this period they were checked for general physical health and suitability as test animals. The animals were housed in stock cages and were permitted a standard laboratory diet plus water ad libitum except during the 16-hour period immediately prior to oral intubation, when food was withheld.

Selected groups of four male albino rats each were administered the undiluted test material at dose levels of 900, 1350, 2025 and 3038mg per kilogram of body weight. All doses were administered directly into the stomachs of the rats using a hypodermic syringe equipped with a ball-tipped intubating needle.

After oral administration of the test material, the rats were housed individually in suspended, wire-mesh cages and observed during the following 14 days. A necropsy was conducted on any animal which died during the study and on all of the remaining animals at the end of the observation period.

The acute oral medium lethal dose ($LD_{50}$) was calculated using the techniques described in the following references:

Weil, Carrol S; Tables for Convenient Calculation of Median-Effective Dose ($LD_{50}$ or $ED_{50}$) and Instructions in Their Use. *Biometrics,* Sept. 1951.

Thompson, William R.; Use of Moving Averages and Interpolation to Estimate Medium-Effective Dose. *Bact. Rev.,* Nov., 1947.

Thompson, William R. and Weil, Carrol S.; On the Construction of Tables for Moving Average Interpolation. *Biometrics,* March, 1952.

The $LD_{50}$ value for the mono-n-octyltin compound test is 2.48 g per kilogram of weight, which is considerably higher than the 1.00 g per kilogram value for the corresponding di-n-octyltin compound. A higher $LD_{50}$ value is indicative of a lower toxicity level.

A second feeding study was conducted for a period of 13 weeks using beagle dogs to determine the maximum concentration of a preferred mono-n-octyltin stabilizer of this invention that can be present in the food of these animals without causing any observable adverse effects on the general health and condition of the internal organs. This concentration level is referred to as the "no-effect level" by the United States Food and Drug Administration.

The criteria employed to determine the absence of toxicological effects included general appearance, health, growth and food intake of the animals; blood analyses for enzyme activity and serum protein; urine analysis to determine kidney damage; change in weight of internal organs and presence of the tin compound in the kidneys, bones, brain, liver and blood.

A stabilizer of this invention, mono-n-octyltin S,S',S"-tris(isooctyl mercaptoacetate), was added to the food consumed by the dogs in amounts of 0, 100, 300 and 1,000 parts per million. At the end of the 13 week test period the dogs were sacrificed and autopsies performed. The no-effect level was found to be 300 parts per million, which is unexpectedly high for an organotin compound. Unfortunately, no data points were taken between 300 and 1,000ppm to determine where, above 300ppm, an effect is detected.

A 13-week feeding study was done on fifty male and fifty female weanling albino rats to determine the effect of dietary levels of 0, 30, 100, 300 and 1,000 parts per million of mono-n-octyltin-S,S',S"-tris(isooctylmercaptoacetate). No distinct deleterious effects were found; the only changes consisted of an increase in the relative weights of the kidneys in males at 1,000ppm accompanied by slightly increased granularity of the cytoplasm of the epithelial cells of the proximal tubules in the kidneys; no changes in renal functions were observed. It was concluded that the no effect level of mono-n-octyltin-tris(isooctylmercaptoacetate) in the diet of rats for 13 weeks may be placed at 300ppm.

EXAMPLE IV

This example demonstrates the efficacy of mono-n-octyltin-S,S',S"-tris(isooctyl mercaptoacetate) as a stabilizer for vinyl chloride polymers.

The test samples employed in the following heat stability tests were prepared using a formulation containing (1) 100 parts of a vinyl chloride homopolymer exhibiting an inherent viscosity of 0.84 as determined using ASTM test method No. 1243-60(a) and available under the trade name Geon 110x223, (2) 18.5 parts of an acrylonitrile-butadient-styrne terpolymer (Blendex 401), (3) 0.5 part of calcium stearate, (4) 0.5 parts of a low molecular weight oxidized polyethylene wax exhibiting a viscosity of 200 centipoises at 140° C., a softening point of 104° C. and an acid number of 15, (5) 0.1 part of Alizarin Irozol blue dye and (6) 2.0 parts mono-n-octyltin S,S',S"-tris(isooctyl mercaptoacetate). The resultant mixture was blended for five minutes on a 2-roll differential speed mill wherein the roll temperature was 177° C. The continuous sheet which formed around one of the rolls was removed and cut into squares measuring about 1 inch (2.54cm) along each side. The color of the test samples was visually evaluated after which they were placed in a curculating air oven heated to a temperature of 204° C. Samples were removed at 5-minute intervals and their color visually rated. At this relatively high temperature the samples required between 20 and 25 minutes of heating to darken completely to a black color. By contrast, an unstabilized polymer composition would turn black during the milling operation and adhere to the mill rolls.

The following color ratings were observed during the heat treatment.
Initial Color following milling—off white
After 5 minutes of heating—slight yellowness
After 10 minutes of heating—slight yellowness
After 15 minutes of heating—yellow
After 20 minutes of heating—yellow-brown
After 25 minutes of heating—black

EXAMPLE V

This example demonstrates the heat stability imparted to a vinyl chloride homopolymer by combinations of a mono-n-octyltin compound and the corresponding di-n-octyltin compound. Test samples were prepared using the procedure described in the preceding Example IV and the following formulation:

|  | Parts (by weight) |
|---|---|
| Vinyl chloride homopolymer (Geon 103-EPO) | 100.0 |
| Acrylic polymer impact modifier (KMO641) | 12.0 |
| Carboxylic ester wax (Wax E) | 1.0 |
| Stabilizer | as specified |

The heat stability of the test samples was evaluated using yellowness index values measured using a Macbeth model MC1500S colormeter. The yellowness index is a function of the amount of yellow light reflected from the test sample, and is read directly from the colormeter.

The colors of the test samples were evaluated after milling and following residence times of 10, 20, 30, 40, 50 and 60 minutes in an oven heated to 190° C. The yellowness index values obtained are recorded in the following table. The stabilizers employed were mono-n-octyltin-S,S',S''-tris(isooctyl mercaptoacetate), di-n-octyltin-S,S'-bis(isooctyl mercaptoacetate) and mixtures of these compounds containing up to 46% of the di-n-octyltin compound. The relative concentrations of mono- and di-n-octyltin compounds and the total stabilizer concentrations were selected so as to maintain the tin content in all the test samples constant.

| YELLOWNESS INDEX OF POLYMER SAMPLES | | | | | | | |
|---|---|---|---|---|---|---|---|
| mono-octyltin compound (parts) | di-octyltin compound (parts) | Heat Exposure Time @ 190° C. (Minutes) | | | | | |
|  |  | 0 | 10 | 20 | 30 | 40 | 50 |
| 0 | 1.5 | 14.22 | 16.94 | 27.99 | 44.49 | 85.36 | 111.97 |
| 0.17 | 1.35 | 16.60 | 17.51 | 20.69 | 31.20 | 79.28 | 108.33 |
| 0.43 | 1.13 | 14.73 | 17.78 | 20.41 | 34.06 | 75.27 | 94.99 |
| 0.85 | 0.75 | 14.95 | 17.83 | 23.51 | 48.81 | 75.13 | 99.91 |

The foregoing data demonstrate that the samples containing 0.17 and 0.43 parts of the monooctyltin compound exhibited substantially less discoloration, i.e. a lower yellowness index, following 20 and 30 minutes of heating than samples containing none or higher concentrations of the monooctyltin compound. At 40 and 50 minute exposure periods, improvement is seen in the samples containing 0.43 and 0.85 parts of mono-n-octyltin compounds. Further, at exposive times above 10 minutes combinations of mono- and di-n-octyltin compounds display improved heat stability when compared with the di-n-octyltin compound alone.

What is claimed is:

1. A packaged foodstuff, comprising a food or beverage sealedly packaged within a shaped article packaging material which comprises a stabilized food grade vinyl halide polymer composition, said polymer composition comprising a nonhazardous effective stabilizing amount of a stabilizer which comprises more than 5% by weight of a monoalkyltin compound having the formula n-$C_8H_{17}Sn(SCH_2COOR)_3$ wherein R is a linear or branched alkyl group of 8 carbon atoms and said compound being individually devoid of such contaminants and exhibiting such acute, chronic and no-effect toxicity levels and extractability values as to satisfy FDA Toxicity Quotient criteria.

2. The packaged foodstuff as defined by claim 1, said vinyl halide polymer comprising a homopolymer or copolymer of vinyl chloride.

3. The packaged foodstuff as defined by claim 2, said monoalkyltin compound having an acute oral toxicity of greater than 1.00 gram per kilogram of body weight, a maximum extraction from polyvinyl chloride by foodstuffs of less than 1 part per million, and a no-effect toxicity level for dogs of 300 parts per million per kilogram of foodstuff.

4. The packaged foodstuff as defined by claim 3, said polymer composition further comprising an auxiliary food grade stabilizer.

5. The packaged foodstuff as defined by claim 4, said polymer composition comprising a nonhazardous effective stabilizing amount of said monoalkyltin compound in admixture with di-n-octyltin-S,S'-bis(isooctylmercaptoacetate) auxiliary stabilizer.

6. The packaged foodstuff as defined by claim 5, said admixture containing up to about 75% by weight of said auxiliary stabilizer.

7. The packaged foodstuff as defined by claim 3, said polymer composition further comprising at least one antioxidant, plasticizer, impact modifying polymer, lubricant, ultra-violet absorber, dye, or mixture thereof.

8. The packaged foodstuff as defined by claim 3, wherein said monoalkyltin compound is mono-n-octyltin-S,S',S''-tris(isooctylmercaptoacetate).

9. The packaged foodstuff as defined by claim 3, wherein said monoalkyltin compound is mono-n-octyltin-S,S',S''-tris(2-ethylhexylmercaptoacetate).

10. The packaged foodstuff as defined by claim 3, said shaped article packaging material comprising a film.

11. The packaged foodstuff as defined by claim 3, said shaped article packaging material comprising a bottle.

12. The packaged foodstuff as defined by claim 3, said shaped article packaging material comprising a tray.

13. The packaged foodstuff as defined by claim 3, said monoalkyltin compound having a purity of at least 95% by weight.

14. The packaged foodstuff as defined by claim 3, said effective stabilizing amount ranging from about 0.15 to 5 parts by weight per 100 parts by weight of said vinyl chloride polymer.

15. The packaged foodstuff as defined by claim 14, said effective stabilizing amount ranging from about 1 to 4 parts by weight per 100 parts by weight of said vinyl chloride polymer.

16. The packaged foodstuff as defined by claim 5, wherein said monoalkyltin compound is mono-n-octyltin-S,S',S''-tris(isooctylmercaptoacetate).

17. The packaged foodstuff as defined by claim 5, wherein said monoalkyltin compound is mono-n-octyltin-S,S',S''-tris(2-ethylhexylmercaptoacetate).

18. The packaged foodstuff as defined by claim 4, said polymer composition comprising a nonhazardous effective stabilizing amount of said monoalkyltin compound in admixture with a dialkyltin compound having the formula $(n\text{-}C_8H_{17})_2Sn(SCH_2COOR')_2$ wherein $R'$ is a linear or branched alkyl group of 8 carbon atoms.

19. The packaged foodstuff as defined by claim 1, said stabilizer comprising at least 30% by weight of said monoalkyltin compound.

20. The packaged foodstuff as defined by claim 6, said stabilizer comprising at least 30% by weight of said monoalkyltin compound.

* * * * *